(12) United States Patent
Zhong et al.

(10) Patent No.: US 11,275,141 B2
(45) Date of Patent: Mar. 15, 2022

(54) MAGNETIC RESONANCE DIFFUSION TENSOR IMAGING METHOD AND DEVICE, AND FIBER TRACKING METHOD AND DEVICE

(71) Applicant: Siemens Healthineers Ltd., Shanghai (CN)

(72) Inventors: Jianhui Zhong, Zhejiang (CN); Mu Lin, Shanghai (CN); Yi Sun, Shanghai (CN)

(73) Assignee: Siemens Healthcare GmbH, Erlangen (DE)

( * ) Notice: Subject to any disclaimer, the term of this patent is extended or adjusted under 35 U.S.C. 154(b) by 349 days.

(21) Appl. No.: 16/582,507

(22) Filed: Sep. 25, 2019

(65) Prior Publication Data

US 2020/0096592 A1    Mar. 26, 2020

(30) Foreign Application Priority Data

Sep. 25, 2018  (CN) .......................... 201811117026.9

(51) Int. Cl.
*G06T 7/00* (2017.01)
*G01R 33/563* (2006.01)
(Continued)

(52) U.S. Cl.
CPC ........ *G01R 33/56341* (2013.01); *A61B 5/055* (2013.01); *A61B 5/7267* (2013.01);
(Continued)

(58) Field of Classification Search
CPC . G01R 33/56341; A61B 5/055; A61B 5/7267; A61B 5/4029; G06N 3/04;
(Continued)

(56) References Cited

U.S. PATENT DOCUMENTS

2018/0092559 A1* 4/2018 Wybo ....................... A61B 5/24
2018/0322635 A1* 11/2018 Guo ..................... G06K 9/3233
2020/0374615 A1* 11/2020 Anderson .............. A61B 5/055

OTHER PUBLICATIONS

Golkov, Vladimir et al. "q-Space Deep Learning: Twelve-Fold Shorter and Model-Free Diffusion MRI Scans" IEEE Transactions on Medical Imaging, vol. 35, No. 5, pp. 1344-1351, May 2016 // XP011607959; ISSN: 0278-0062; DOI:10.1109/TMI.2016.2551324, [retrieved on Apr. 29, 2016], Abstract, Sections I.A., II. and III.; figures 2,6.

* cited by examiner

*Primary Examiner* — Ping Y Hsieh
(74) *Attorney, Agent, or Firm* — Schiff Hardin LLP

(57) ABSTRACT

A magnetic resonance diffusion tensor imaging method and corresponding device. The method includes acquiring omnidirectionally sampled diffusion weighted images of a plurality of training samples; performing diffusion tensor model fitting and undersampling for the omnidirectionally sampled diffusion weighted images of each training sample to obtain an omnidirectionally sampled diffusion tensor image and an undersampled diffusion weighted image; training a deep learning network, with the omnidirectionally sampled diffusion tensor images of the plurality of training samples as training targets and the undersampled diffusion weighted images as training data; acquiring undersampled diffusion weighted images of a target object; and inputting the undersampled diffusion weighted images of target objects into the trained deep learning network to obtain the predicted omnidirectionally sampled diffusion tensor images of the target objects. Also, a fiber tracking method and corresponding device.

14 Claims, 4 Drawing Sheets

(51) Int. Cl.
*G06N 3/04* (2006.01)
*G06N 3/08* (2006.01)
*A61B 5/00* (2006.01)
*A61B 5/055* (2006.01)

(52) U.S. Cl.
CPC ............... *G06N 3/04* (2013.01); *G06N 3/08* (2013.01); *G06T 7/97* (2017.01); *A61B 5/4029* (2013.01); *G06T 2207/10092* (2013.01); *G06T 2207/20081* (2013.01); *G06T 2207/20084* (2013.01)

(58) Field of Classification Search
CPC ... G06N 3/08; G06T 7/97; G06T 2207/10092; G06T 2207/20081; G06T 2207/20084; G06T 11/003
See application file for complete search history.

101
Acquire omnidirectionally sampled diffusion weighted images of plurality of training samples.

102
Perform diffusion tensor model fitting for the omnidirectionally sampled diffusion weighted images of each training sample to obtain an omnidirectionally sampled diffusion tensor image of said training sample.

103
Perform undersampling for the omnidirectionally sampled diffusion weighted images of each training sample in the diffusion weighted direction dimension to obtain the undersampled diffusion weighted image of said training sample.

104
Train deep learning network, with the omnidirectionally sampled diffusion tensor images of said plurality of training samples as training targets and the undersampled diffusion weighted images of said plurality of training samples as training data.

105
Acquire undersampled diffusion weighted images of a target object.

106
Input the undersampled diffusion weighted images of the target object into a trained deep learning network to obtain an omnidirectionally sampled diffusion tensor image predicted by the deep learning network and use the predicted omnidirectionally sampled diffusion tensor image as the diffusion tensor image of the target object.

Figure 2

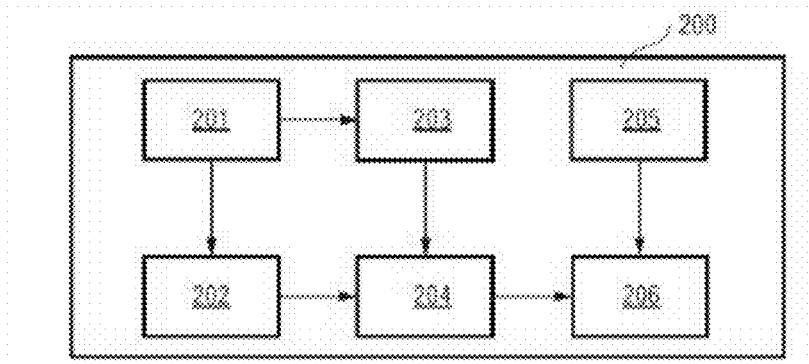

MAGNETIC RESONANCE DIFFUSION TENSOR IMAGING METHOD AND DEVICE, AND FIBER TRACKING METHOD AND DEVICE

TECHNICAL FIELD

The present disclosure relates to the technical field of the magnetic resonance imaging system, and in particular relates to a magnetic resonance diffusion tensor imaging method and device, a fiber tracking method and device, and a storage medium.

BACKGROUND

Diffusion tensor imaging (DTI), a special form of magnetic resonance imaging (MRI), has widely been applied in clinics because it can non-invasively show the morphological structure of a tissue. It plays an important role in the diagnoses and treatments of diseases in brains, cardiac muscle fibers, spinal cords, kidneys, muscles and peripheral nerves, and it is applied the most widely in the diagnoses and treatments of cerebral neuropathy.

Diffusion tensor tractography (DTT), also known as fiber tracking (FT), is the further development of DTI and can show the running of 3-dimensional nerve tracts. DTT provides guidance for clinical surgeries, prevents important nerve tract branches from being damaged during surgeries, and thus guarantees the prognosis of patients. However, DTT requires a large amount of data acquisition time to guarantee the accuracy of fiber tracking, and therefore the clinical application of DTT is restricted.

SUMMARY

In the embodiments of the present disclosure, a magnetic resonance diffusion tensor imaging method and device are proposed in one aspect, a fiber tracking method and device are proposed in a further aspect, and in addition, a storage medium is proposed. They are used to improve the efficiency of magnetic resonance diffusion tensor imaging and the efficiency of fiber tracking and lower the cost.

A magnetic resonance diffusion tensor imaging method proposed in the embodiments of the present disclosure comprises: acquiring omnidirectionally sampled diffusion weighted images of a plurality of training samples; performing diffusion tensor model fitting for the omnidirectionally sampled diffusion weighted images of each training sample to obtain an omnidirectionally sampled diffusion tensor image of said training sample and performing undersampling for the omnidirectionally sampled diffusion weighted images of said training sample in the diffusion weighted direction dimension to obtain the undersampled diffusion weighted image of said training sample; training a deep learning network, with the omnidirectionally sampled diffusion tensor images of said plurality of training samples as training targets and the undersampled diffusion weighted images of said plurality of training samples as training data; acquiring undersampled diffusion weighted images of a target object; inputting the undersampled diffusion weighted images of said target object into a trained deep learning network to obtain an omnidirectionally sampled diffusion tensor image predicted by said deep learning network and using said predicted omnidirectionally sampled diffusion tensor image as the diffusion tensor image of said target object.

In one embodiment, said acquiring the omnidirectionally sampled diffusion weighted images of said plurality of training samples comprises acquiring the omnidirectionally sampled diffusion weighted image output from a magnetic resonance scanner for each training sample, or acquiring the omnidirectionally sampled diffusion weighted images with the set b-value of a plurality of training samples from the public data of the HCP.

In one embodiment, said b-value is a b-value corresponding to the imaging requirement in clinical applications.

A fiber tracking method proposed in the embodiments of the present disclosure comprises: acquiring undersampled diffusion weighted images of a target object; inputting the undersampled diffusion weighted images into the trained deep learning network to obtain an omnidirectionally sampled diffusion tensor image predicted by said deep learning network and using said omnidirectionally sampled diffusion tensor image as the diffusion tensor image of said target object; performing fiber tracking for the diffusion tensor image of said target object.

In one embodiment, said trained deep learning network is obtained in the following way: acquiring omnidirectionally sampled diffusion weighted images of a plurality of training samples; performing diffusion tensor model fitting for the omnidirectionally sampled diffusion weighted images of each training sample to obtain an omnidirectionally sampled diffusion tensor image of said training sample and performing undersampling for the omnidirectionally sampled diffusion weighted images of said training sample in the diffusion weighted direction dimension to obtain the undersampled diffusion weighted image of said training sample; training a deep learning network, with the omnidirectionally sampled diffusion tensor images of said plurality of training samples as training targets and the undersampled diffusion weighted images of said plurality of training samples as training data.

In one embodiment, said acquiring the omnidirectionally sampled diffusion weighted images of said plurality of training samples comprises acquiring the omnidirectionally sampled diffusion weighted image output from a magnetic resonance scanner for each training sample, or acquiring the omnidirectionally sampled diffusion weighted images with the set b-value of a plurality of training samples from the public data of the HCP.

A magnetic resonance diffusion tensor imaging device proposed in the embodiments of the present disclosure comprises: a totally sampled diffusion weighted image acquisition module, configured to acquire the omnidirectionally sampled diffusion weighted images of a plurality of training samples; a totally sampled diffusion tensor image generation module, configured to perform diffusion tensor model fitting for the omnidirectionally sampled diffusion weighted images of each training sample to obtain an omnidirectionally sampled diffusion tensor image of said training sample; an undersampled diffusion weighted image generation module, configured to perform undersampling for the omnidirectionally sampled diffusion weighted images of each training sample in the diffusion weighted direction dimension to obtain the undersampled diffusion weighted image of said training sample; a training module, configured to train a deep learning network, with the omnidirectionally sampled diffusion tensor images of said plurality of training samples as training targets and the undersampled diffusion weighted images of said plurality of training samples as training data; an undersampled diffusion weighted image acquisition module, configured to acquire the undersampled diffusion weighted images of a target object; a totally sampled diffusion tensor image prediction module, configured to input the undersampled diffusion weighted images of said target object into a trained deep learning network to obtain an omnidirectionally sampled diffusion tensor image predicted by said deep learning network and use said predicted omnidirectionally sampled diffusion tensor image as the diffusion tensor image of said target object.

In one embodiment, said totally sampled diffusion weighted image acquisition module acquires the omnidirectionally sampled diffusion weighted image output from a magnetic resonance scanner for each training sample, or acquires the omnidirectionally sampled diffusion weighted images with the set b value of a plurality of training samples from the public data of the HCP.

A fiber tracking device proposed in the embodiments of the present disclosure comprises: an undersampled diffusion weighted image acquisition module, configured to acquire the undersampled diffusion weighted images of a target object; a totally sampled diffusion tensor image prediction module, configured to input the undersampled diffusion weighted images into a trained deep learning network to obtain an omnidirectionally sampled diffusion tensor image predicted by said deep learning network and use said predicted omnidirectionally sampled diffusion tensor image as the diffusion tensor image of said target object; a tracking module, configured to perform fiber tracking for the diffusion tensor image of said target object.

In one embodiment, the fiber tracking device further comprises: a totally sampled diffusion weighted image acquisition module, configured to acquire the omnidirectionally sampled diffusion weighted images of a plurality of training samples; a totally sampled diffusion tensor image generation module, configured to perform diffusion tensor model fitting for the omnidirectionally sampled diffusion weighted images of each training sample to obtain an omnidirectionally sampled diffusion tensor image of said training sample; an undersampled diffusion weighted image generation module, configured to perform undersampling for the omnidirectionally sampled diffusion weighted images of each training sample in the diffusion weighted direction dimension to obtain the undersampled diffusion weighted image of said training sample; a training module, configured to train a deep learning network, with the omnidirectionally sampled diffusion tensor images of said plurality of training samples as training targets and the undersampled diffusion weighted images of said plurality of training samples as training data.

In one embodiment, said totally sampled diffusion weighted image acquisition module acquires the omnidirectionally sampled diffusion weighted image output from a magnetic resonance scanner for each training sample, or acquires the omnidirectionally sampled diffusion weighted images with the set b-value of a plurality of training samples from the public data of the HCP.

A magnetic resonance diffusion tensor imaging device further proposed in the embodiments of the present disclosure comprises at least one memory and at least one processor, wherein said at least one memory is configured to store computer programs, and said at least one processor is configured to implement the computer program stored in said at least one memory to execute the magnetic resonance diffusion tensor imaging method in any of the above-mentioned embodiments.

A fiber tracking device further proposed in the embodiments of the present disclosure comprises at least one memory and at least one processor, wherein said at least one memory is configured to store computer programs, and said at least one processor is configured to implement the computer program stored in said at least one memory to execute the fiber tracking method in any of the above-mentioned embodiments.

A computer readable storage medium proposed in the embodiments of the present disclosure stores a computer program, and said computer program can be executed by a processor to realize the magnetic resonance diffusion tensor imaging method or fiber tracking method in any of the above-mentioned embodiments.

From the above-mentioned technical solutions, it can be seen that in the embodiments of the present disclosure, the omnidirectionally sampled diffusion weighted images of a plurality of training samples are first acquired, then omnidirectionally sampled diffusion tensor images are generated by use of the traditional processing method and the omnidirectionally sampled diffusion weighted images are undersampled to obtain undersampled diffusion weighted images, and after that, a deep learning network is trained with the omnidirectionally sampled diffusion tensor images of a plurality of training samples as training targets and the undersampled diffusion weighted images as training data to obtain a trained deep learning network. After that, when a magnetic resonance diffusion tensor image is generated for a target object, the omnidirectionally sampled diffusion weighted images of the target object do not need to be acquired. Instead, only undersampled diffusion weighted images in a few directions need to be acquired and input into a trained deep learning network, and then an omnidirectionally sampled diffusion tensor image is directly output. The process greatly reduces the data acquisition time and also guarantees the imaging quality of magnetic resonance diffusion tensor images, thus improving the imaging efficiency of magnetic resonance diffusion tensor images.

In addition, when the omnidirectionally sampled diffusion weighted images of a plurality of training samples are acquired, the omnidirectionally sampled diffusion weighted images with the set b-value are directly acquired from the public data of the HCP. This can fully utilize the existing resources and save the cost of re-acquiring diffusion weighted images through a magnetic resonance scanner.

In addition, by using the omnidirectionally sampled diffusion weighted image with the b-value corresponding to the imaging requirement in clinical applications, the trained deep learning network can directly be applied in clinics, and the deep learning network can be updated dynamically as the b-value corresponding to the clinical imaging requirement changes.

Further, the trained deep learning network can be applied to fiber tracking to improve the efficiency of fiber tracking.

BRIEF DESCRIPTION OF THE DRAWINGS

The following will describe in detail the preferred embodiments of the present disclosure by reference to the drawings so that those skilled in the art can have a clearer idea of the above-mentioned and other characteristics and advantages of the present disclosure.

FIG. 1 is an exemplary flowchart of a magnetic resonance diffusion tensor imaging method in the embodiments of the present disclosure.

FIG. 2 is an exemplary structural diagram of a magnetic resonance diffusion tensor imaging device in the embodiments of the present disclosure.

DESCRIPTION OF REFERENCE NUMERALS IN THE DRAWINGS

Figure 3:
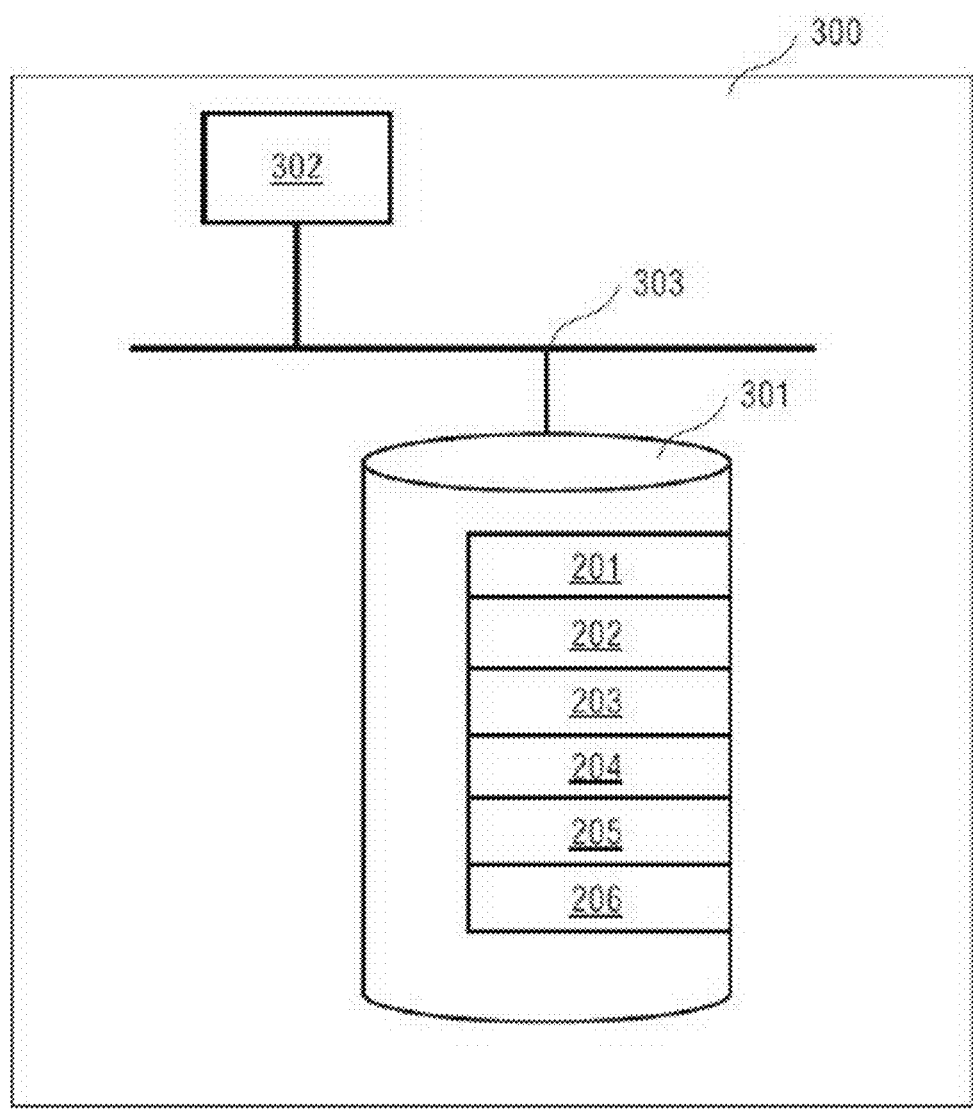
FIG. 3 is an exemplary structural diagram of another magnetic resonance diffusion tensor imaging device in the embodiments of the present disclosure.

| Reference numeral | Meaning |
| --- | --- |
| 100, 400 | Method |
| 101-106, 401-403 | Steps |
| 200, 300, 500, 600 | Device |
| 201 | Totally sampled diffusion weighted image acquisition module |
| 202 | Totally sampled diffusion tensor image generation module |
| 203 | Undersampled diffusion weighted image generation module |
| 204 | Training module |
| 205, 501 | Undersampled diffusion weighted image acquisition module |
| 206, 502 | Totally sampled diffusion tensor image prediction module |
| 301, 601 | Memory |
| 302, 602 | Processor |
| 303, 603 | Bus |
| 503 | Tracking module |

DETAILED DESCRIPTION

Considering that fiber tracking requires a high image quality of magnetic resonance diffusion tensor imaging in the embodiments of the present disclosure, the diffusion weighted image generated from as many scans as possible should be acquired before a magnetic resonance diffusion tensor image is acquired. For the convenience of description, a diffusion weighted image satisfying the requirement for the preset high number of scans (for example, higher than or equal to a first preset number of scans) or high number of scanning directions (for example, higher than or equal to the first preset number of scanning directions) is called an omnidirectionally sampled diffusion weighted image. Then, a diffusion tensor model fitting is performed for said omnidirectionally sampled diffusion weighted image to obtain an omnidirectionally sampled diffusion tensor image, and then fiber tracking is performed on the basis of the omnidirectionally sampled diffusion tensor image.

However, considering that an omnidirectionally sampled diffusion weighted image requires the magnetic resonance imaging system to perform many scans, the efficiency is low and the cost is high. In the embodiments of the present disclosure, the above-mentioned omnidirectionally sampled diffusion weighted images are used as training targets, undersampling is performed for the omnidirectionally sampled diffusion weighted images in the diffusion weighted direction dimension to obtain the undersampled diffusion weighted images, and the undersampled diffusion weighted images are used as training data to train a deep learning network on the basis of the theory of the convolutional neural network to obtain a deep learning model. After that, the undersampled diffusion weighted images of target objects such as test objects or diagnostic objects can directly be acquired and input into the trained deep learning model to predict the omnidirectionally sampled diffusion tensor images of target objects. Finally, fiber tracking is performed for the diffusion tensor images predicted by the deep learning network. In this document, for the convenience of description, a diffusion weighted image satisfying the requirement for the preset low number of scans (for example, lower than or equal to a second preset number of scans) or low number of scanning directions (for example, lower than or equal to a second preset number of scanning directions) is called an undersampled diffusion weighted image. Wherein, the first preset number of scans is greater than the second preset number of scans, and the first preset number of scanning directions is greater than the second preset number of scanning directions. In the embodiments of the present disclosure, each time a scan is performed for a diffusion weighted image, the diffusion weighted direction will be changed, and therefore the number of scans is equal to the number of scanning directions.

To make clearer the objectives, technical solutions, and advantages of the present disclosure, the following gives embodiments to further describe the present disclosure in detail.

FIG. 1 is an exemplary flowchart of a magnetic resonance diffusion tensor imaging method (100) in the embodiments of the present disclosure. As shown in FIG. 1, the method (100) can comprise the following steps:

Step 101: Acquire omnidirectionally sampled diffusion weighted images of a plurality of training samples.

In this step, the omnidirectionally sampled diffusion weighted images can be obtained by using a magnetic resonance scanner to scan each object as a training sample, or can be images with the set b-value of a plurality of training samples acquired from the public data of the HCP.

Wherein, considering the magnetic resonance diffusion tensor imaging method in the present embodiment is mainly applied to related applications in clinics, for example, fiber tracking, the b-value is the b-value corresponding to the clinical imaging requirement. For example, images with different b-values exist in the HCP data, and different b-values correspond to sampling in different numbers of directions. For example, b-values such as 1000 s/mm$^2$, 3000 s/mm$^2$, 5000 s/mm$^2$ and 10000 s/mm$^2$ exist, and the corresponding numbers of directions are 64, 64, 128 and 128, respectively. In the present embodiment, considering that a b-value of 800 s/mm$^2$ to 1500 s/mm$^2$ is often adopted in current clinical applications, the omnidirectionally sampled diffusion weighted images with a b-value of 1000 s/mm$^2$ can be acquired from the HCP. Of course, with the development of magnetic resonance imaging technology, the b-value adopted in clinical applications may change. Accordingly, the b-value of the omnidirectionally sampled diffusion weighted image acquired in this step will also change. In this way, on the one hand, the deep learning network can directly be applied to clinics, and on the other hand, the deep learning network can be updated dynamically as the b-value corresponding to the clinical imaging requirement changes.

Step 102: Perform a diffusion tensor model fitting for the omnidirectionally sampled diffusion weighted images of each training sample to obtain an omnidirectionally sampled diffusion tensor image of said training sample.

In this step, the diffusion tensor model fitting for the omnidirectionally sampled diffusion weighted images of said training sample can be performed in many ways. An algorithm can automatically be realized according to the formula and then the diffusion tensor model fitting is performed with the volume pixel as a unit, or the diffusion tensor model fitting is realized by use of available open-source software. The way in which the diffusion tensor model fitting is realized is not restricted here.

Wherein, a diffusion tensor image can include parameters such as fractional anisotropy (FA), mean diffusivity (MD), axial diffusivity (DA), radial diffusivity (DR) and eigenvector, wherein the eigenvector is configured to indicate the direction of a fiber.

Step 103: Perform undersampling for the omnidirectionally sampled diffusion weighted images of each training sample in the diffusion weighted direction dimension to obtain the undersampled diffusion weighted image of said training sample.

In this step, the omnidirectionally sampled diffusion weighted images in Step 101 are mainly undersampled, for example some diffusion weighted images are randomly extracted from said omnidirectionally sampled diffusion weighted images to form undersampled diffusion weighted images. For example, when the above-mentioned omnidirectionally sampled diffusion weighted images sampled in 64 directions are undersampled, diffusion weighted images in 6 directions can be randomly extracted to obtain undersampled diffusion weighted image data. Wherein, the 6 directions can be evenly distributed directions or unevenly distributed directions.

Wherein, only one group or more groups of undersampled diffusion weighted images can be acquired for a training sample, depending on the actual requirement.

Step 104: Train a deep learning network, with the omnidirectionally sampled diffusion tensor images of said plurality of training samples as training targets and the undersampled diffusion weighted images of said plurality of training samples as training data.

In this step, the deep learning network can be trained on the basis of the theory of the neural network to obtain a trained deep learning network. When the deep learning network is trained, a correspondence relationship is established between the omnidirectionally sampled diffusion weighted images and the undersampled diffusion weighted images of the same training sample.

Step 105 and Step 106 mainly relate to the imaging process in which the above-mentioned trained deep learning network is applied to realize omnidirectionally sampled diffusion tensor images when target objects (for example, patients) are actually scanned.

Step 105: Acquire undersampled diffusion weighted images of a target object.

In this step, the target object can be a test object for testing a trained deep learning network or a diagnostic object for diagnosing diseases in clinical applications.

It can be seen that in the embodiments of the present disclosure, when magnetic resonance imaging is used for a target object, only a low number of scans for undersampling, instead of a high number of scans for omnidirectional sampling is required, for example scan-sampling can be performed only in 6 directions.

Step 106: Input the undersampled diffusion weighted images of said target object into a trained deep learning network to obtain an omnidirectionally sampled diffusion tensor image predicted by said deep learning network and use said predicted omnidirectionally sampled diffusion tensor image as the diffusion tensor image of said target object.

The magnetic resonance diffusion tensor imaging method in the embodiments of the present disclosure is described above. The magnetic resonance diffusion tensor imaging device in the embodiments of the present disclosure will be described in detail below. The magnetic resonance diffusion tensor imaging device in the embodiments of the present disclosure can be used to realize the magnetic resonance diffusion tensor imaging method in the embodiments of the present disclosure. For the details not described in the embodiments of the magnetic resonance diffusion tensor imaging device of the present disclosure, please refer to the corresponding description in the embodiments of the magnetic resonance diffusion tensor imaging method of the present disclosure. These details are omitted here.

FIG. 2 is an exemplary structural diagram of a magnetic resonance diffusion tensor imaging device (200) in the embodiments of the present disclosure. As shown in FIG. 2, the magnetic resonance diffusion tensor imaging device (200) can comprise a totally sampled diffusion weighted image acquisition module (201), a totally sampled diffusion tensor image generation module (202), an undersampled diffusion weighted image generation module (203), a training module (204), an undersampled diffusion weighted image acquisition module (205) and a totally sampled diffusion tensor image prediction module (206).

Wherein, the totally sampled diffusion weighted image acquisition module (201) is configured to acquire the omnidirectionally sampled diffusion weighted images of a plurality of training samples. In this specific implementation, said totally sampled diffusion weighted image acquisition module (201) acquires the omnidirectionally sampled diffusion weighted image output from a magnetic resonance scanner for each training sample, or acquires the omnidirectionally sampled diffusion weighted images with the set b-value of a plurality of training samples from the public data of the HCP.

The totally sampled diffusion tensor image generation module (202) is configured to perform diffusion tensor model fitting for the omnidirectionally sampled diffusion weighted images of each training sample to obtain an omnidirectionally sampled diffusion tensor image of said training sample.

The undersampled diffusion weighted image generation module (203) is configured to perform undersampling for the omnidirectionally sampled diffusion weighted images of each training sample in the diffusion weighted direction dimension to obtain the undersampled diffusion weighted image of said training sample.

The training module (204) is configured to train a deep learning network, with the omnidirectionally sampled diffusion tensor images of said plurality of training samples as training targets and the undersampled diffusion weighted images of said plurality of training samples as training data.

The undersampled diffusion weighted image acquisition module (205) is configured to acquire the undersampled diffusion weighted images of a target object.

The totally sampled diffusion tensor image prediction module (206) is configured to input the undersampled diffusion weighted images of said target object into a trained deep learning network to obtain an omnidirectionally sampled diffusion tensor image predicted by said deep learning network and use said predicted omnidirectionally sampled diffusion tensor image as the diffusion tensor image of said target object.

FIG. 3 is an exemplary structural diagram of another magnetic resonance diffusion tensor imaging device (300) in the embodiments of the present disclosure. As shown in FIG. 3, the magnetic resonance diffusion tensor imaging device (300) can comprise at least one memory (301) and at least one processor (302). Of course, the magnetic resonance diffusion tensor imaging device (300) can further comprise some other components, for example communication ports. These components can communicate with each other through a bus (303).

Wherein, at least one memory (301) is configured to store a computer program. In an embodiment, it can be considered that the computer program comprises the modules of the magnetic resonance diffusion tensor imaging device shown in FIG. 2, namely the totally sampled diffusion weighted image acquisition module (201), the totally sampled diffusion tensor image generation module (202), the undersampled diffusion weighted image generation module (203), the training module (204), the undersampled diffusion weighted image acquisition module (205) and the totally sampled diffusion tensor image prediction module (206).

In addition, at least one memory (301) can further store an operating system. The operating system includes but is not limited to the Android operating system, Symbian operating system, Windows operating system and Linux operating system.

At least one processor (302) is configured to implement the computer program stored in at least one memory (301) to execute said magnetic resonance imaging method described in FIG. 1 based on the function of at least one port receiving data. The processor (302) can be a central processing unit (CPU), a processing unit/module, an application specific integrated circuit (ASIC), a logic module or a programmable array.

Figure 4:
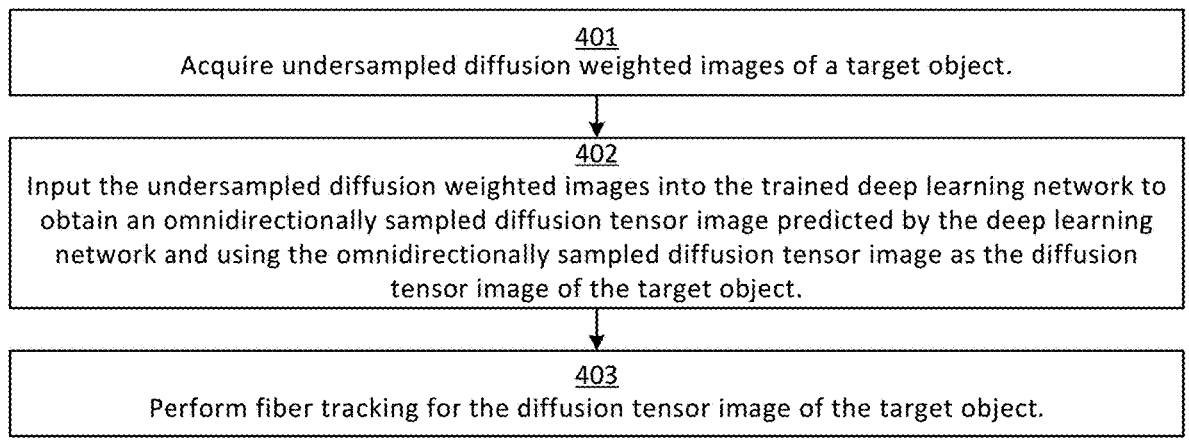
FIG. 4 is an exemplary flowchart of a fiber tracking method in the embodiments of the present disclosure.

FIG. 4 is an exemplary flowchart of a fiber tracking method (400) in the embodiments of the present disclosure. As shown in FIG. 4, the method (400) can comprise the following steps:

Step 401: Acquire undersampled diffusion weighted images of a target object.

In this step, when magnetic resonance imaging is used for a target object, only a low number of scans for undersampling, instead of a high number of scans for omnidirectional sampling is required, for example, sampling can be performed only in 6 directions.

Step 402: Input the undersampled diffusion weighted images into the trained deep learning network to obtain an omnidirectionally sampled diffusion tensor image predicted by said deep learning network and using said omnidirectionally sampled diffusion tensor image as the diffusion tensor image of said target object.

Step 403: Perform fiber tracking for the diffusion tensor image of said target object.

Wherein, said trained deep learning network can be obtained through Steps 101 to 104 of the method shown in FIG. 1, namely acquire omnidirectionally sampled diffusion weighted images of a plurality of training samples; perform diffusion tensor model fitting for the omnidirectionally sampled diffusion weighted images of each training sample to obtain an omnidirectionally sampled diffusion tensor image of said training sample and perform undersampling for the omnidirectionally sampled diffusion weighted images of said training sample in the diffusion weighted direction dimension to obtain the undersampled diffusion weighted image of said training sample; train a deep learning network, with the omnidirectionally sampled diffusion tensor images of said plurality of training samples as training targets and the undersampled diffusion weighted images of said plurality of training samples as training data.

The fiber tracking method in the embodiments of the present disclosure is described above. The fiber tracking device in the embodiments of the present disclosure will be described in detail below. The fiber tracking device in the embodiments of the present disclosure can be used to realize the fiber tracking method in the embodiments of the present disclosure. For the details not described in the embodiments of the fiber tracking device of the present disclosure, please refer to the corresponding description in the embodiments of the fiber tracking method of the present disclosure. These details are omitted here.

Figure 5:
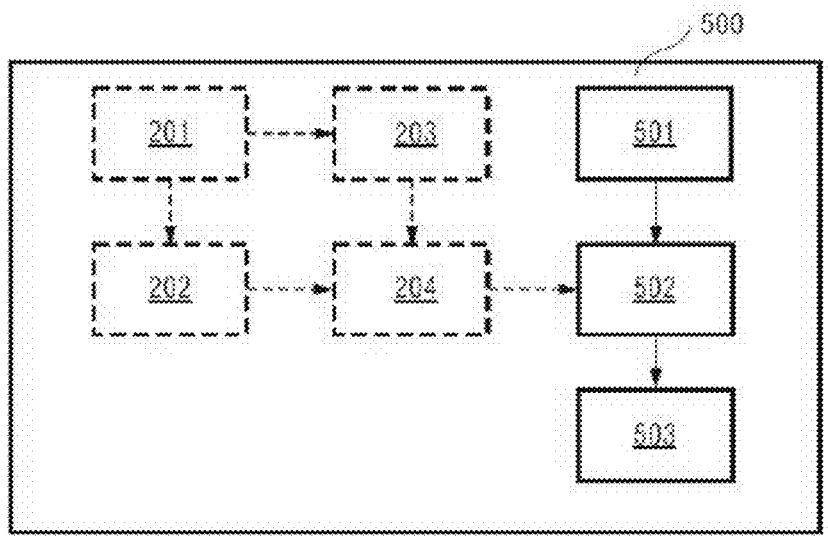
FIG. 5 is an exemplary structural diagram of a fiber tracking device in the embodiments of the present disclosure.

FIG. 5 is an exemplary structural diagram of a fiber tracking device (500) in the embodiments of the present disclosure. As shown in FIG. 5, the fiber tracking device (500) can comprise an undersampled diffusion weighted image acquisition module (501), a totally sampled diffusion tensor image prediction module (502) and a tracking module (503) in the solid-line boxes.

Wherein, the undersampled diffusion weighted image acquisition module (501) is configured to acquire the undersampled diffusion weighted images of a target object.

The totally sampled diffusion tensor image prediction module (502) is configured to input the undersampled diffusion weighted images into a trained deep learning network to obtain an omnidirectionally sampled diffusion tensor image predicted by said deep learning network and use said predicted omnidirectionally sampled diffusion tensor image as the diffusion tensor image of said target object.

The tracking module (503) is configured to perform fiber tracking for the diffusion tensor image of said target object.

In other embodiments, the fiber tracking device can further comprise the totally sampled diffusion weighted image acquisition module (201), the totally sampled diffusion tensor image generation module (202), the undersampled diffusion weighted image generation module (203) and the training module (204) in FIG. 2, as shown in the dotted-line boxes in FIG. 5.

Figure 6:
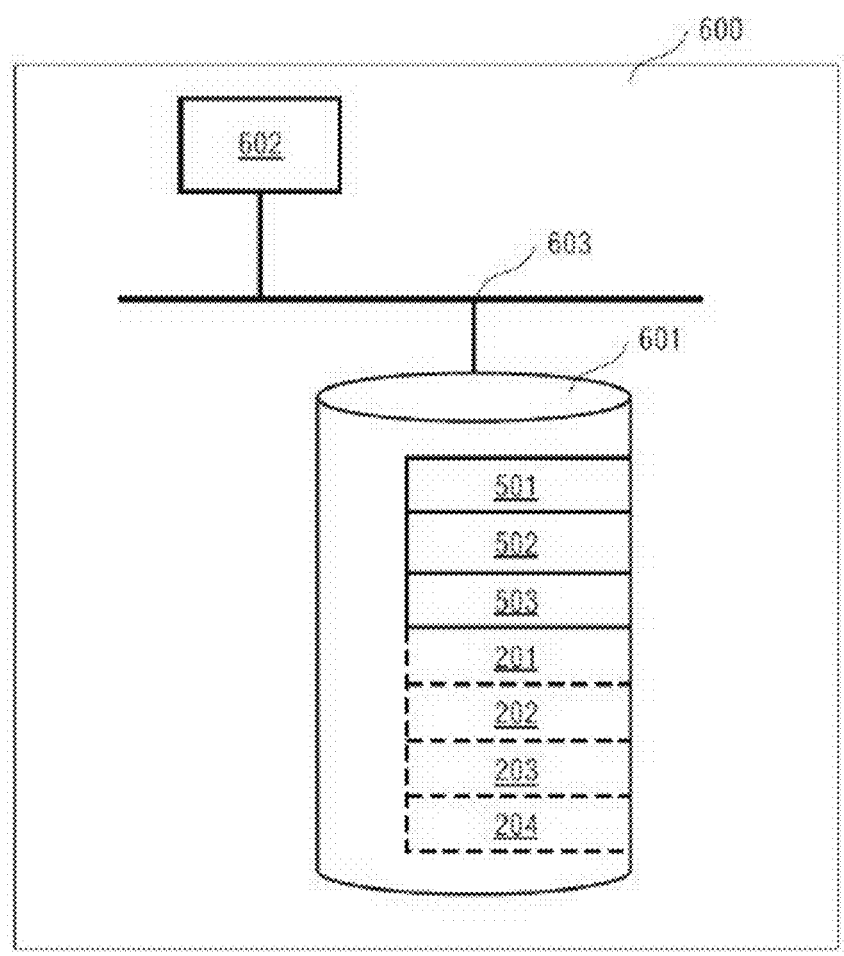
FIG. 6 is an exemplary structural diagram of another fiber tracking device in the embodiments of the present disclosure.

FIG. 6 is an exemplary structural diagram of another fiber tracking device (600) in the embodiments of the present disclosure. As shown in FIG. 6, the fiber tracking device (600) can comprise at least one memory (601) and at least one processor (602). Of course, the fiber tracking device (600) can further comprise some other components, for example a communication port. These components can communicate with each other through a bus (603).

Wherein, at least one memory (601) is configured to store a computer program. In an embodiment, it can be considered that the computer program comprises the modules of the fiber tracking devices shown in FIG. 5, namely the undersampled diffusion weighted image acquisition module (501), the totally sampled diffusion tensor image prediction module (502) and the tracking module (503). In other embodiments, the computer program can further comprise the totally sampled diffusion weighted image acquisition module (201), the totally sampled diffusion tensor image generation module (202), the undersampled diffusion weighted image generation module (203) and the training module (204).

In addition, at least one memory (601) can further store an operating system. The operating system includes but is not limited to the Android operating system, Symbian operating system, Windows operating system and Linux operating system.

At least one processor (602) is configured to implement the computer program stored in at least one memory (601) to execute the fiber tracking method described in FIG. 4 based on the function of at least one port receiving data. The processor (602) can be a central processing unit (CPU), a processing unit/module, an application specific integrated circuit (ASIC), a logic module or a programmable array.

It should be noted that not all steps or modules in the above-mentioned processes and structural diagrams are required, and some steps or modules can be ignored, depending on the actual requirements. The execution sequence of the steps is not fixed and can be adjusted as required. The partition of the modules is a functional partition for the convenience of description. In the practical implementation, the function of a module can be realized by a plurality of modules, and the functions of a plurality of modules can be realized by one module and these modules can be located in the same equipment or can be located in different equipment.

It should be understood that the hardware modules in different embodiments can be realized mechanically or electronically. For example, a hardware module can comprise specially designed permanent circuits or logic devices (for example, application-specific processors such as field programmable gate array (FPGA) or ASIC) to complete specific operations. A hardware module can also comprise programmable logic devices or circuits (for example, general processors or other programmable processors) temporarily configured by software to perform specific operations. Whether a hardware module is realized mechanically, or by use of a dedicated permanent circuit or a temporarily configured circuit (for example, configured by software) can depend on the considerations of cost and time.

The present disclosure further provides a machine readable storage medium, in which instructions allowing a machine to execute the methods described in the present disclosure are stored. Specifically, a system or device equipped with a storage medium can be provided. Software program codes which can realize the function in any of above-mentioned embodiments are stored in the storage medium and the computer (or CPU or MPU) of the system or device can read out and execute the program codes stored in the storage medium. In addition, through the instructions based on the program codes, the operating system on the computer can complete practical operations in whole or in part. In addition, the program codes read out of a storage medium can be written into the memory in the expansion board in a computer or can be written into a memory in an expansion unit connected to the computer, and then the instructions based on the program codes let the CPU installed on the expansion board or expansion unit execute practical operations in whole or in part to realize the function in any of the above-mentioned embodiments. Storage media used to provide program codes include floppy disk, hard disk, magneto-optical disk, compact disk (for example, compact disk read-only memory (CD-ROM), compact disk recordable (CD-R), compact disk-rewritable (CD-RW), digital video disk-read only memory (DVD-ROM), digital versatile disk-random access memory (DVD-RAM), digital versatile disk-rewritable (DVD+RW)), magnetic tape, non-volatile memory card, and read-only memory (ROM). Alternatively, the program codes can be downloaded from the server computer over a communication network.

From the above-mentioned technical solutions, it can be seen that in the embodiments of the present disclosure, the omnidirectionally sampled diffusion weighted images of a plurality of training samples are first acquired, then omnidirectionally sampled diffusion tensor images are generated by use of the traditional processing method and the omnidirectionally sampled diffusion weighted images are undersampled to obtain undersampled diffusion weighted images, and after that, a deep learning network is trained with the omnidirectionally sampled diffusion tensor images of a plurality of training samples as training targets and the undersampled diffusion weighted images as training data to obtain a trained deep learning network. After that, when a magnetic resonance diffusion tensor image is generated for a target object, the omnidirectionally sampled diffusion weighted images of the target object do not need to be acquired. Instead, only undersampled diffusion weighted images in a few directions need to be acquired and input into a trained deep learning network, and then an omnidirectionally sampled diffusion tensor image is directly output. The process greatly reduces the data acquisition time and also guarantees the imaging quality of magnetic resonance diffusion tensor images, thus improving the imaging efficiency of magnetic resonance diffusion tensor images.

In addition, when the omnidirectionally sampled diffusion weighted images of a plurality of training samples are acquired, the omnidirectionally sampled diffusion weighted images with the set b-value are directly acquired from the public data of the HCP. This can fully utilize the existing resources and save the cost of re-acquiring diffusion weighted images through a magnetic resonance scanner.

In addition, by using the omnidirectionally sampled diffusion weighted image with the b-value corresponding to the imaging requirement in clinical applications, the trained deep learning network can be applied directly in clinics, and the deep learning network can be updated dynamically as the b-value corresponding to the clinical imaging requirement changes.

Further, the trained deep learning network can be applied to fiber tracking to improve the efficiency of fiber tracking.

The above-mentioned embodiments are only preferred embodiments of the present disclosure, but are not used to restrict the present disclosure. Without departing from the spirit and principle of the present disclosure, modifications, equivalent replacements, and improvements should all fall within the scope of protection of the present disclosure.

The invention claimed is:

1. A magnetic resonance diffusion tensor imaging method, comprising:
    acquiring omnidirectionally sampled diffusion weighted images of a plurality of training samples;
    performing diffusion tensor model fitting for the omnidirectionally sampled diffusion weighted images of each training sample to obtain an omnidirectionally sampled diffusion tensor image of the training sample, and performing undersampling for the omnidirectionally sampled diffusion weighted images of the training sample in the diffusion weighted direction dimension to obtain the undersampled diffusion weighted image of the training sample;
    training a deep learning network, with the omnidirectionally sampled diffusion tensor images of the plurality of training samples as training targets and the undersampled diffusion weighted images of the plurality of training samples as training data;
    acquiring undersampled diffusion weighted images of a target object; and
    inputting the undersampled diffusion weighted images of the target object into a trained deep learning network to obtain an omnidirectionally sampled diffusion tensor image predicted by the deep learning network and using the predicted omnidirectionally sampled diffusion tensor image as the diffusion tensor image of the target object.

2. The magnetic resonance diffusion tensor imaging method as claimed in claim 1, wherein the acquiring the omnidirectionally sampled diffusion weighted images of the plurality of training samples comprises:
    acquiring the omnidirectionally sampled diffusion weighted image output from a magnetic resonance scanner for each training sample, or acquiring the omnidirectionally sampled diffusion weighted images with a set b-value of a plurality of training samples from the public data of the Human Connectome Project (HCP).

3. The magnetic resonance diffusion tensor imaging method as claimed in claim 2, wherein the b-value is a b-value corresponding to the imaging requirement in clinical applications.

4. A magnetic resonance diffusion tensor imaging device, comprising:
   at least one memory; and
   at least one processor,
   wherein the at least one memory is configured to store computer programs, and the at least one processor is configured to implement a computer program stored in the at least one memory to execute the magnetic resonance diffusion tensor imaging method as claimed in claim 1.

5. A non-transitory computer readable storage medium, storing a computer program, wherein the computer program can be executed by a processor to realize the magnetic resonance diffusion tensor imaging method as claimed in claim 1.

6. A fiber tracking method, comprising:
   acquiring undersampled diffusion weighted images of a target object;
   inputting the undersampled diffusion weighted images into a trained deep learning network to obtain an omnidirectionally sampled diffusion tensor image predicted by the deep learning network, and using the omnidirectionally sampled diffusion tensor image as the diffusion tensor image of the target object; and
   performing fiber tracking for the diffusion tensor image of the target object.

7. The fiber tracking method as claimed in claim 6, wherein the trained deep learning network is obtained by:
   acquiring omnidirectionally sampled diffusion weighted images of a plurality of training samples;
   performing diffusion tensor model fitting for the omnidirectionally sampled diffusion weighted images of each training sample to obtain an omnidirectionally sampled diffusion tensor image of the training sample, and performing undersampling for the omnidirectionally sampled diffusion weighted images of the training sample in the diffusion weighted direction dimension to obtain the undersampled diffusion weighted image of the training sample; and
   training a deep learning network, with the omnidirectionally sampled diffusion tensor images of the plurality of training samples as training targets and the undersampled diffusion weighted images of the plurality of training samples as training data.

8. The fiber tracking method as claimed in claim 7, wherein the acquiring the omnidirectionally sampled diffusion weighted images of the plurality of training samples comprises:
   acquiring the omnidirectionally sampled diffusion weighted image output from a magnetic resonance scanner for each training sample, or acquiring the omnidirectionally sampled diffusion weighted images with the a b-value of a plurality of training samples from the public data of the HCP.

9. A fiber tracking device, comprising:
   at least one memory; and
   at least one processor,
   wherein the at least one memory is configured to store computer programs, and the at least one processor is configured to implement the computer program stored in the at least one memory to execute the fiber tracking method as claimed in claim 6.

10. A magnetic resonance diffusion tensor imaging device, comprising:
    a totally sampled diffusion weighted image acquisition module circuit configured to acquire the omnidirectionally sampled diffusion weighted images of a plurality of training samples;
    a totally sampled diffusion tensor image generation module circuit configured to perform diffusion tensor model fitting for the omnidirectionally sampled diffusion weighted images of each training sample to obtain an omnidirectionally sampled diffusion tensor image of the training sample;
    an undersampled diffusion weighted image generation module circuit configured to perform undersampling for the omnidirectionally sampled diffusion weighted images of each training sample in the diffusion weighted direction dimension to obtain the undersampled diffusion weighted image of the training sample;
    a training module circuit configured to train a deep learning network, with the omnidirectionally sampled diffusion tensor images of the plurality of training samples as training targets and the undersampled diffusion weighted images of the plurality of training samples as training data;
    an undersampled diffusion weighted image acquisition module circuit configured to acquire the undersampled diffusion weighted images of a target object; and
    a totally sampled diffusion tensor image prediction module circuit configured to input the undersampled diffusion weighted images of the target object into a trained deep learning network to obtain an omnidirectionally sampled diffusion tensor image predicted by the deep learning network and use the predicted omnidirectionally sampled diffusion tensor image as the diffusion tensor image of the target object.

11. The magnetic resonance diffusion tensor imaging device as claimed in claim 10, wherein the totally sampled diffusion weighted image acquisition module circuit acquires the omnidirectionally sampled diffusion weighted image output from a magnetic resonance scanner for each training sample, or acquires the omnidirectionally sampled diffusion weighted images with a set b-value of a plurality of training samples from the public data of the HCP.

12. A fiber tracking device, comprising:
    an undersampled diffusion weighted image acquisition module circuit configured to acquire the undersampled diffusion weighted images of a target object;
    a totally sampled diffusion tensor image prediction module circuit configured to input the undersampled diffusion weighted images into a trained deep learning network to obtain an omnidirectionally sampled diffusion tensor image predicted by the deep learning network and use the predicted omnidirectionally sampled diffusion tensor image as the diffusion tensor image of the target object; and
    a tracking module circuit configured to perform fiber tracking for the diffusion tensor image of the target object.

13. The fiber tracking device as claimed in claim 12, further comprising:

a totally sampled diffusion weighted image acquisition module circuit configured to acquire the omnidirectionally sampled diffusion weighted images of a plurality of training samples;

a totally sampled diffusion tensor image generation module circuit configured to perform diffusion tensor model fitting for the omnidirectionally sampled diffusion weighted images of each training sample to obtain an omnidirectionally sampled diffusion tensor image of the training sample;

an undersampled diffusion weighted image generation module circuit configured to perform undersampling for the omnidirectionally sampled diffusion weighted images of each training sample in the diffusion weighted direction dimension to obtain the undersampled diffusion weighted image of the training sample; and a training module circuit configured to train a deep learning network, with the omnidirectionally sampled diffusion tensor images of the plurality of training samples as training targets and the undersampled diffusion weighted images of the plurality of training samples as training data.

14. The fiber tracking device as claimed in claim 13, wherein the totally sampled diffusion weighted image acquisition module circuit is configured to acquire the omnidirectionally sampled diffusion weighted image output from a magnetic resonance scanner for each training sample, or is configured to acquire the omnidirectionally sampled diffusion weighted images with 1 set b-value of a plurality of training samples from the public data of the HCP.

* * * * *